(12) United States Patent
Hayashi et al.

(10) Patent No.: US 10,321,884 B2
(45) Date of Patent: Jun. 18, 2019

(54) SUPPORTING DEVICE AND X-RAY DIAGNOSTIC APPARATUS

(71) Applicant: TOSHIBA MEDICAL SYSTEMS CORPORATION, Otawara-shi (JP)

(72) Inventors: Yoshiyasu Hayashi, Nasushiobara (JP); Shigeyuki Ishii, Nasushiobara (JP); Kousuke Sakaue, Nasushiobara (JP); Takuya Sakaguchi, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 690 days.

(21) Appl. No.: 14/885,388

(22) Filed: Oct. 16, 2015

(65) Prior Publication Data

US 2016/0038110 A1 Feb. 11, 2016

Related U.S. Application Data

(63) Continuation of application No. PCT/JP2014/059764, filed on Apr. 2, 2014.

(30) Foreign Application Priority Data

Apr. 18, 2013 (JP) .................................. 2013-087784

(51) Int. Cl.
*A61B 6/00* (2006.01)
*H05K 5/02* (2006.01)

(52) U.S. Cl.
CPC ............... *A61B 6/462* (2013.01); *A61B 6/46* (2013.01); *A61B 6/461* (2013.01); *A61B 6/464* (2013.01);
(Continued)

(58) Field of Classification Search
CPC ......... A61B 6/4441; A61B 6/46; A61B 6/461; A61B 6/462; A61B 6/464; A61B 6/465; A61B 6/467; A61B 6/54; A61B 6/542
(Continued)

(56) References Cited

U.S. PATENT DOCUMENTS 4,894,855 A * 1/1990 Kresse .................... A61B 6/032
378/189
5,008,921 A * 4/1991 Kaul .................... A61B 6/4405
378/193
(Continued)

FOREIGN PATENT DOCUMENTS

JP 2-63814 5/1990
JP 4-253846 A 9/1992
(Continued)

OTHER PUBLICATIONS

International Search Report dated Jun. 3, 2014 in PCT/JP2014/059764 filed Apr. 2, 2014 (with English translation).
(Continued)

*Primary Examiner* — Allen C. Ho
(74) *Attorney, Agent, or Firm* — Oblon, McClelland, Maier & Neustadt, L.L.P.

(57) ABSTRACT

A supporting device according to an embodiment includes a holder, a supporter, and a controller. The holder holds a user terminal that includes a detection surface that detects an input operation by an operator. The supporter is connected to the holder and is movably provided so as to locate a user terminal at a predetermined position, the user terminal being held by the holder. The controller fixes the supporter in a state where the supporter is located at a predetermined position when the detection surface detects the input operation.

10 Claims, 13 Drawing Sheets

(52) U.S. Cl.
CPC ............... *A61B 6/467* (2013.01); *A61B 6/54* (2013.01); *A61B 6/542* (2013.01); *H05K 5/0204* (2013.01); *A61B 6/4441* (2013.01); *A61B 6/465* (2013.01)

(58) Field of Classification Search
USPC ............ 378/98, 189, 204, 208, 62, 196–198
See application file for complete search history.

(56) References Cited

U.S. PATENT DOCUMENTS

| | | | | |
|---|---|---|---|---|
| 6,200,024 B1* | 3/2001 | Negrelli | ............... | A61B 6/4233 378/196 |
| 6,325,537 B1* | 12/2001 | Watanabe | ............ | A61B 6/4233 378/196 |
| 6,435,715 B1* | 8/2002 | Betz | ................. | A61B 6/4458 378/197 |
| 6,463,121 B1* | 10/2002 | Milnes | ................. | A61B 6/4482 378/62 |
| 6,582,121 B2* | 6/2003 | Crain | ................ | A61B 6/107 378/196 |
| 6,590,958 B2* | 7/2003 | Barber | ................ | A61B 6/107 378/196 |
| 6,764,217 B2* | 7/2004 | Yasuda | ................ | A61B 6/08 378/196 |
| 6,869,217 B2* | 3/2005 | Rasche | ................ | A61B 6/4458 378/197 |
| 7,016,454 B2* | 3/2006 | Wärnberg | ............ | A61B 6/02 378/197 |
| 7,029,177 B2* | 4/2006 | Watanabe | ............ | A61B 6/06 378/197 |
| 7,250,922 B2* | 7/2007 | Sakaniwa | ............ | A61B 6/4464 345/1.1 |
| 7,401,977 B2* | 7/2008 | Graumann | ............ | A61B 6/4441 378/197 |
| 7,410,138 B2* | 8/2008 | Parsons | ................. | A61G 15/10 248/278.1 |
| 7,441,953 B2* | 10/2008 | Banks | ................. | A61B 5/1038 378/197 |
| 7,821,778 B2* | 10/2010 | Herman | ................ | A61B 5/00 361/679.01 |
| 8,021,045 B2* | 9/2011 | Foos | .................... | A61B 6/4405 378/198 |
| 8,252,049 B2* | 8/2012 | Maschke | ................. | A61B 6/12 606/108 |
| 8,338,810 B2* | 12/2012 | Hoernig | ................. | A61B 6/107 250/505.1 |
| 8,449,183 B2* | 5/2013 | Seimiya | ................ | A61B 6/4464 378/196 |
| 8,457,713 B2* | 6/2013 | Kagermeier | ......... | A61B 6/4405 378/63 |
| 8,459,867 B2* | 6/2013 | Muller | ................. | A61B 6/4464 378/197 |
| 8,594,271 B2* | 11/2013 | Sakaguchi | ............ | A61B 6/4441 378/4 |
| 8,622,614 B2* | 1/2014 | Carmichael | .......... | A61B 6/4266 378/198 |
| 8,678,648 B2* | 3/2014 | Lalena | ................ | A61B 6/4266 378/114 |
| 8,678,649 B2* | 3/2014 | Bechard | ................. | A61B 6/4405 378/198 |
| 8,755,492 B2* | 6/2014 | Lee | ........................ | H05G 1/02 378/115 |
| 8,781,068 B2* | 7/2014 | Noda | .................... | A61B 6/4233 378/19 |
| 8,827,554 B2* | 9/2014 | Lalena | .................... | A61B 6/46 378/206 |
| 8,849,370 B2* | 9/2014 | Bouvier | .............. | A61B 6/102 600/407 |
| 8,876,380 B2* | 11/2014 | Mizrahi | ............... | A61B 5/0422 378/203 |
| 8,899,834 B2* | 12/2014 | Barker | ................ | A61B 6/4405 250/370.09 |
| 8,961,011 B2* | 2/2015 | Lalena | ................ | A61B 6/4405 378/197 |
| 8,971,482 B2* | 3/2015 | Bailey | ..................... | A61B 6/03 378/20 |
| 8,977,021 B2* | 3/2015 | Kang | .................... | G16H 50/50 382/128 |
| 9,044,186 B2* | 6/2015 | Ma | ....................... | A61B 6/4035 |
| 9,084,582 B2* | 7/2015 | Omura | ................. | A61B 6/4405 |
| 9,107,694 B2* | 8/2015 | Hendriks | ................. | A61B 6/12 |
| 9,192,343 B2* | 11/2015 | Eklund | ................... | A61B 6/06 |
| 9,204,853 B2* | 12/2015 | Foos | ........................ | A61B 6/50 |
| 9,241,680 B2* | 1/2016 | Kyöstilä | ................. | A61B 6/04 |
| 9,265,470 B2* | 2/2016 | Simmons | ............... | A61B 6/447 |
| 9,295,438 B2* | 3/2016 | Omura | .................. | A61B 6/4405 |
| 9,339,247 B2* | 5/2016 | Jarva | ..................... | A61B 6/14 |
| 9,357,974 B2* | 6/2016 | Foos | ...................... | A61B 6/4405 |
| 9,413,961 B2* | 8/2016 | Welsh | .................... | A61B 6/4405 |
| 9,414,802 B2* | 8/2016 | Urbon | .................. | A61B 6/4283 |
| 9,478,018 B2* | 10/2016 | Rongen | ................ | A61B 6/4441 |
| 9,498,173 B2* | 11/2016 | Yamada | ............... | A61B 6/4405 |
| 9,521,983 B2* | 12/2016 | Jang | ..................... | A61B 6/4429 |
| 9,532,756 B2* | 1/2017 | Wakai | ..................... | A61B 5/00 |
| 9,572,544 B2* | 2/2017 | O'Dea | ................... | A61B 6/547 |
| 9,613,289 B2* | 4/2017 | Sakaguchi | ........... | G06K 9/4604 |
| 9,622,716 B2* | 4/2017 | Jarva | ...................... | A61B 6/14 |
| 9,649,074 B2* | 5/2017 | Simon | .................... | A61B 6/025 |
| 9,655,575 B2* | 5/2017 | Park | ...................... | A61B 6/4233 |
| 9,655,585 B2* | 5/2017 | Watanabe | ............. | A61B 6/542 |
| 9,668,710 B2* | 6/2017 | Ruijters | ............... | A61B 6/5235 |
| 9,693,437 B2* | 6/2017 | Simmons | ............... | G01N 23/04 |
| 9,693,746 B2* | 7/2017 | Ancar | .................... | A61B 6/08 |
| 9,775,684 B2* | 10/2017 | Tuma | ..................... | A61B 90/37 |
| 9,833,209 B2* | 12/2017 | Belei | .................... | A61B 6/4441 |
| 9,851,708 B2* | 12/2017 | Heijman | ............... | G05B 19/19 |
| 9,872,320 B2* | 1/2018 | Jun | ........................ | G16H 40/63 |
| 9,875,531 B2* | 1/2018 | Goossen | ............... | G06T 5/50 |
| 9,888,895 B2* | 2/2018 | Klingenbeck | .......... | A61B 6/504 |
| 9,888,898 B2* | 2/2018 | Imagawa | ............... | A61B 6/5247 |
| 9,892,233 B2* | 2/2018 | Zeilinger | ............... | G16H 40/40 |
| 9,918,681 B2* | 3/2018 | Wallace | ................ | A61B 6/12 |
| 9,943,276 B2* | 4/2018 | Park | ........................ | A61B 6/461 |
| 10,016,173 B2* | 7/2018 | Foos | ..................... | A61B 6/03 |
| 10,028,788 B2* | 7/2018 | Kang | .................... | A61B 6/4441 |
| 2011/0317816 A1 | 12/2011 | Bechard et al. | | |

FOREIGN PATENT DOCUMENTS

| | | |
|---|---|---|
| JP | 2004-73354 A | 3/2004 |
| JP | 2006-288774 A | 10/2006 |
| JP | 2007-36437 A | 2/2007 |
| JP | 2012-223500 A | 11/2012 |
| JP | 2012-247905 A | 12/2012 |
| WO | 2011/163660 A2 | 12/2011 |

OTHER PUBLICATIONS

Written Opinion dated Jun. 3, 2014 in PCT/JP2014/059764 filed Apr. 2, 2014.

* cited by examiner

SUPPORTING DEVICE AND X-RAY DIAGNOSTIC APPARATUS

CROSS-REFERENCE TO RELATED APPLICATIONS

This application is a continuation of PCT international application Ser. No. PCT/JP2014/059764 filed on Apr. 2, 2014 which designates the United States, incorporated herein by reference, and which claims the benefit of priority from Japanese Patent Application No. 2013-087784, filed on Apr. 18, 2013, the entire contents of which are incorporated herein by reference.

FIELD

Embodiments described herein relate generally to a supporting device and an X-ray diagnostic apparatus.

BACKGROUND

Multiple display devices that display various types of information are conventionally used in clinical practices. For example, in an X-ray angiography system that is used for a diagnosis/treatment of a circulatory system, such as a brain or a heart, displays are provided in an examination room where a surgery is performed on a subject and in an operation room where the X-ray diagnostic apparatus is operated. Furthermore, multiple observers in the examination room and the operation room observe the information that is presented on each of the displays. For example, in the examination room, a doctor who performs a surgery, or the like, observes a transparent image, or the like, that is presented on the display that is provided in the examination room. Furthermore, for example, in the operation room, an operator, or the like, operates the X-ray diagnostic apparatus in accordance with a doctor's command and observes various types of information that is presented on the display that is provided in the operation room.

Furthermore, in recent years, there have been known multiuser-adaptive medical information processing systems in which a server device is connected to multiple user terminals via a communication network. The medical information processing systems include, for example, a known system in which an operating terminal (for example, workstation) that is provided in the operation room is connected to multiple user terminals that are used in the examination room and the operating terminal is operated by the user terminal. However, according to the above-described conventional technology, the operability of the user terminal is sometimes decreased.

DETAILED DESCRIPTION

According to an embodiment, a supporting device includes a holder, a supporter and a controller. The holder is configured to hold a terminal device that includes a detection surface that detects an input operation by an operator. The supporter is configured to be connected to the holder and to be movably provided so as to locate a terminal device at a predetermined position, the terminal device being held by the holder. The controller is configured to fix the supporter in a state where the supporter is located at a predetermined position when the detection surface detects the input operation.

A detailed explanation is given below of an embodiment of a supporting device and an X-ray diagnostic apparatus with reference to the attached drawings. Furthermore, an explanation is given below of, for example, the case where the supporting device according to the present application is applied to an X-ray angiography system.

Figure 1A:
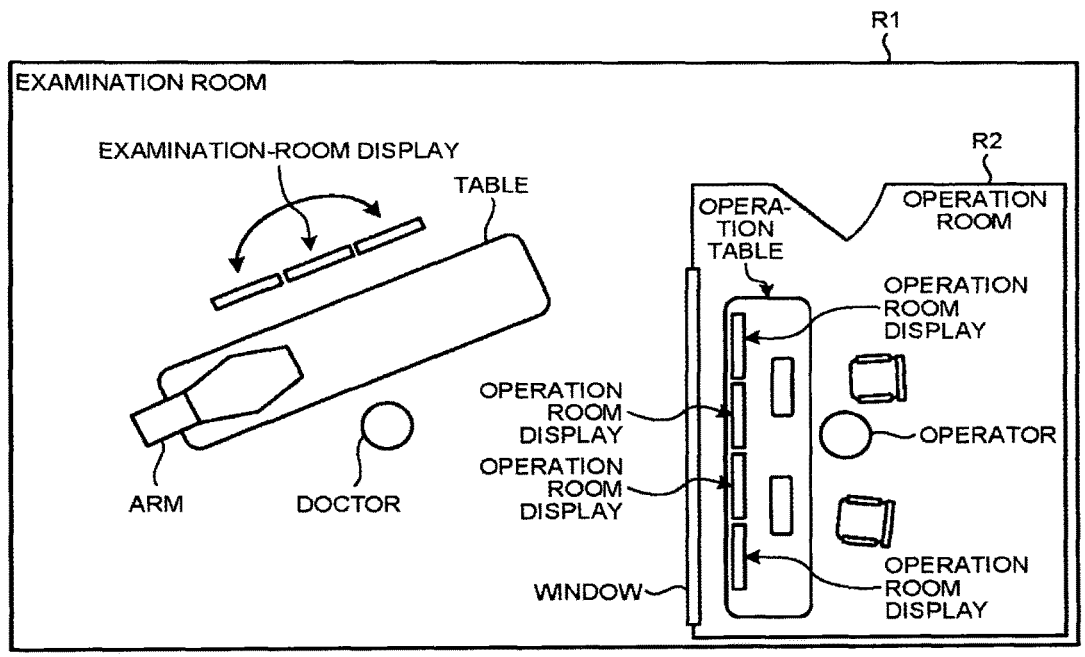
FIG. 1A is a diagram that illustrates an example of an X-ray angiography system according to a first embodiment.
Figure 1B:
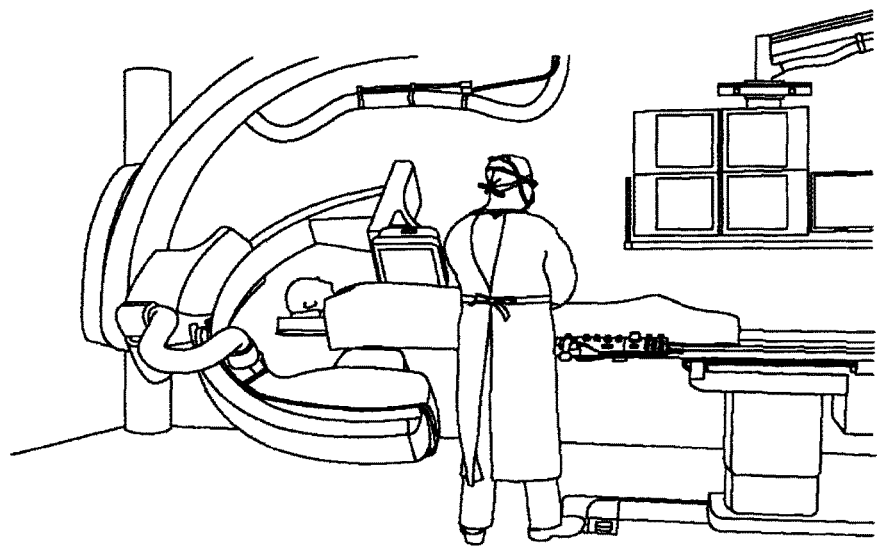
FIG. 1B is a diagram that illustrates an example of the X-ray angiography system according to the first embodiment.

First, an explanation is given, with reference to FIG. 1A and FIG. 1B, of an example of an X-ray angiography system according to a first embodiment. FIG. 1A and FIG. 1B are diagrams that illustrate an example of the X-ray angiography system according to the first embodiment. For example, as illustrated in FIG. 1A, in the X-ray angiography system, an apparatus main body that includes an arm and a table is provided in an examination room R1 where a diagnosis/treatment is conducted on a circulatory system, such as a brain or a heart. Furthermore, an operating terminal that performs an operation to control the apparatus main body is provided in an operation room R2 that is illustrated in FIG. 1A.

Furthermore, multiple examination-room displays and multiple operation-room displays are provided in the examination room R1 and the operation room R2. For example, the examination-room display is observed by a doctor who performs a surgery, a nurse, or the like. Moreover, the operation-room display is observed by an operator who performs an operation to control the apparatus main body.

Here, the medical apparatus according to the first embodiment makes it possible to improve the operability of an operation using a user terminal. In recent years, for example, the technology for conducting a remote control by connecting a user terminal to an operating terminal that is provided in the operation room R2 has started to be applied to the X-ray angiography system that is illustrated in FIG. 1A. For example, the application "Splashtop Touchpad" has started to be used for accessing an operating terminal from a mobile terminal through Wi-Fi (registered trademark) to perform a remote control on the mouse and the keyboard of the operating terminal.

According to the technology, for example, a mobile terminal and an operating terminal are connected via a wireless communication, and the operation received by the mobile terminal is wirelessly received by the operating terminal, whereby the mouse and the keyboard of the operating terminal are remotely controlled. For example, a doctor who is in the examination room R1 uses the touch panel of the mobile terminal as a touch-pad to operate the pointer that is displayed on the examination-room display, thereby performing an input operation on the GUI that is displayed on the examination-room display.

However, in the above system, the operability of the user terminal is sometimes decreased. For example, when a doctor operates the mobile terminal, the doctor often performs a touch operation on the mobile terminal that is held by an assistant. In this case, the assistant holds the mobile terminal each time the doctor operates the mobile terminal, which is inefficient. Therefore, for example, it is possible to use a supporting device that supports the mobile terminal and, in such a case, it is preferable to use a flexible supporting device so as to refrain from interfering during other than an operation. In the case of the flexible supporting device, it is easy to perform an operation to move or remove it; however, because of an insufficient holding force, an adequate operation sometimes can not be performed, and the operability is decreased.

Figure 2:
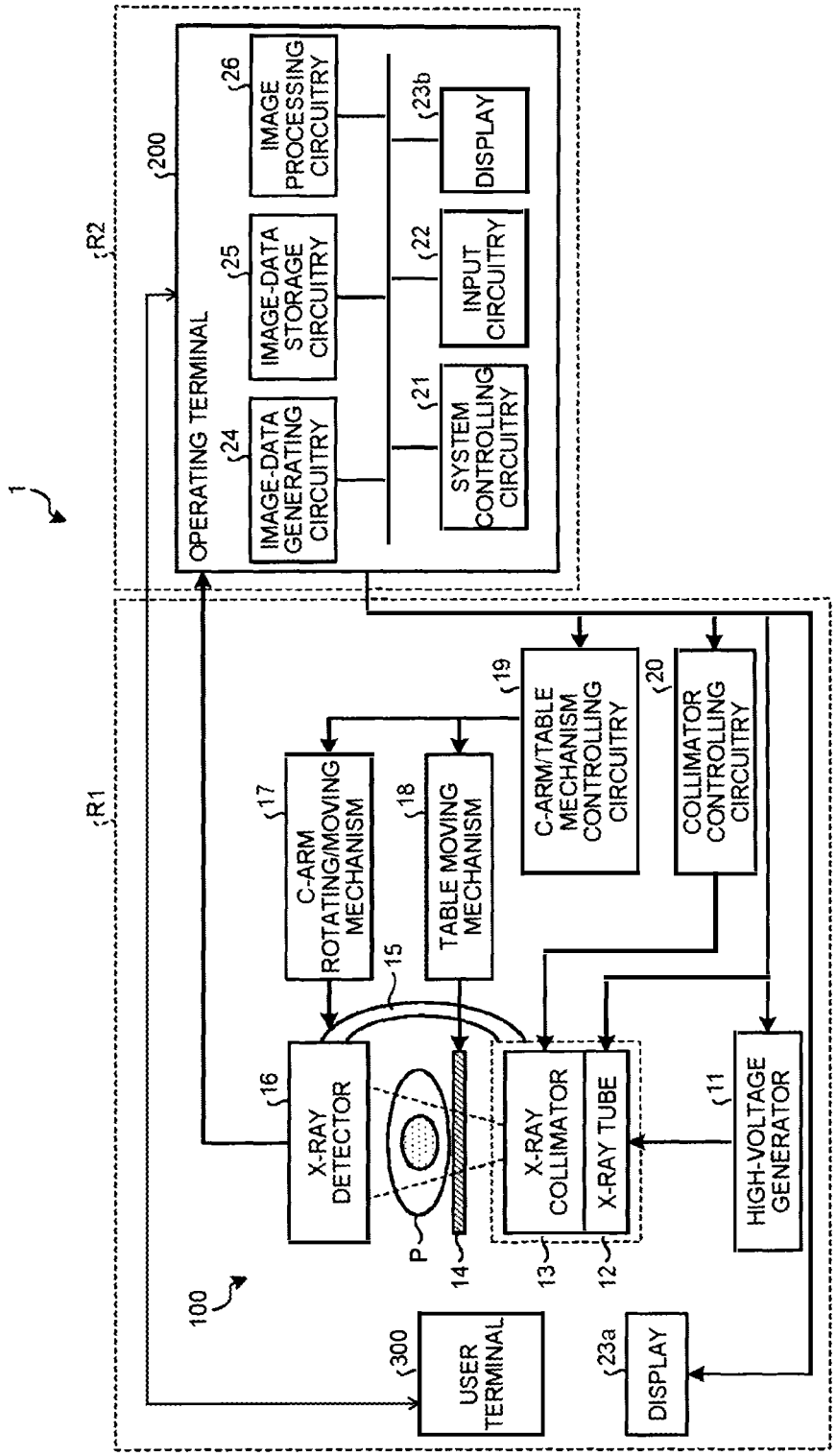
FIG. 2 is a diagram that illustrates an example of the configuration of the X-ray angiography system to which a user terminal according to the first embodiment is applied.

As described above, according to the conventional technology, the operability of a user terminal is sometimes decreased. Hence, in the supporting device according to the first embodiment, a joint section is fixed only during an operation; thus, the operability is improved. A detailed explanation is given below of an embodiment of the supporting device according to the first embodiment. Furthermore, an explanation is first given below of an X-ray angiography system 1 to which the supporting device is applied, and then an explanation is given of the supporting device. FIG. 2 is a diagram that illustrates an example of the configuration of the X-ray angiography system 1 to which the user terminal according to the first embodiment is applied.

As illustrated in FIG. 2, the X-ray angiography system 1 according to the first embodiment includes an apparatus main body 100 and an operating terminal 200. As illustrated in FIG. 2, the apparatus main body 100 includes a high-voltage generator 11, an X-ray tube 12, an X-ray collimator 13, a table 14, a C arm 15, an X-ray detector 16, a C-arm rotating/moving mechanism 17, a table moving mechanism 18, a C-arm/table mechanism controlling circuitry 19, a collimator controlling circuitry 20, and a display 23a, and it is provided in the examination room R1. As illustrated in FIG. 2, the operating terminal 200 includes a system controlling circuitry 21, an input circuitry 22, a display 23b, an image-data generating circuitry 24, an image-data storage circuitry 25, and an image processing circuitry 26, and it is provided in the operation room R2. Furthermore, the operating terminal 200 communicates with a user terminal 300 (or terminal device) and performs an operation in response to the input operation that is received by the user terminal 300.

Here, in FIG. 2, the single user terminal is provided in the examination room R1; however, there is no limitation on the embodiment and, for example, there may be a case where two or more user terminals are provided. Moreover, there may be a case where the user terminals 300 are provided in the examination room R1 and the operation room R2, or there may be a case where it is provided in the operation room. Moreover, although not illustrated, the X-ray angiography system 1 includes an injector, or the like, that injects a contrast media through a catheter that is inserted into a subject P.

Under the control of the system controlling circuitry 21, the high-voltage generator 11 generates a high voltage and supplies the generated high voltage to the X-ray tube 12. The X-ray tube 12 uses the high voltage, which is supplied from the high-voltage generator 11, to generate X-rays.

Under the control of the collimator controlling circuitry 20, the X-ray collimator 13 focuses X-rays, which are generated by the X-ray tube 12, such that they are selectively emitted to the area of interest of the subject P. For example, the X-ray collimator 13 includes four slidable collimator blades. Under the control of the collimator controlling circuitry 20, the X-ray collimator 13 slides the collimator blades to focus X-rays, which are generated by the X-ray tube 12, and emits them to the subject P. Furthermore, the X-ray tube 12 and the X-ray collimator 13 are also collectively referred to as an X-ray tube device. The table 14 is a bed on which the subject P is placed, and it is provided on an undepicted bed. Moreover, the subject P is not included in the apparatus main body 100.

The X-ray detector 16 detects X-rays that are transmitted through the subject P. For example, the X-ray detector 16 includes detecting elements that are arranged in a matrix. Each detecting element converts X-rays, which are transmitted through the subject P, into electric signals, stores them, and transmits the stored electric signals to the image-data generating circuitry 24.

The C arm 15 holds the X-ray tube 12, the X-ray collimator 13, and the X-ray detector 16. The X-ray tube 12 and the X-ray collimator 13 are provided such that they are opposed to the X-ray detector 16 by the C arm 15 with the subject P interposed therebetween.

The C-arm rotating/moving mechanism 17 is the mechanism that rotates and moves the C arm 15, and the table moving mechanism 18 is the mechanism that moves the table 14. The C-arm/table mechanism controlling circuitry 19 controls the C-arm rotating/moving mechanism 17 and the table moving mechanism 18 under the control of the system controlling circuitry 21, thereby adjusting the rotation and movement of the C arm 15 and the movement of the table 14. The collimator controlling circuitry 20 adjusts the numerical aperture of the collimator blades included in the X-ray collimator 13 under the control of the system controlling circuitry 21, thereby controlling the irradiation area of X-rays that are emitted to the subject P.

The image-data generating circuitry 24 generates image data by using electric signals that are converted from X-rays by the X-ray detector 16 and stores the generated image data in the image-data storage circuitry 25. For example, the image-data generating circuitry 24 performs a current/voltage conversion, an analog (A)/digital (D) conversion, or a parallel/serial conversion on electric signals that are received from the X-ray detector 16, thereby generating image data.

Furthermore, the image-data generating circuitry 24 generates an X-ray image from the generated image data and stores the generated X-ray image in the image-data storage circuitry 25. The image-data storage circuitry 25 stores the image data that is generated by the image-data generating circuitry 24.

The image processing circuitry 26 performs various types of image processing on the image data that is stored in the image-data storage circuitry 25. For example, the image processing circuitry 26 processes multiple X-ray images that are stored in the image-data storage circuitry 25 in chronological order, thereby generating a moving image.

The input circuitry 22 receives various commands from an operator who operates the X-ray angiography system 1. For example, the input circuitry 22 includes a mouse, keyboard, button, trackball, joystick, or the like. The input circuitry 22 transfers, to the system controlling circuitry 21, the command that is received from the operator.

The display 23a and the display 23b display the graphical user interface (GUI) for receiving an operator's command, image data that is stored in the image-data storage circuitry 25, or the like. For example, the display 23a is an examination-room display, and the display 23b is an operation-room display. Furthermore, each of the display 23a and the display 23b may include multiple displays. Here, the display 23a and the display 23b display the same contents. For example, the display 23a and the display 23b display a real-time transparent image, a three-dimensional road map (3DRM), or the like. Here, the 3DRM is the image in which a real-time transparent image is superimposed on the projection image that is generated from volume data that is acquired by the apparatus main body 100.

The system controlling circuitry 21 controls the overall operation of the X-ray angiography system 1. For example, the system controlling circuitry 21 controls the high-voltage generator 11 in accordance with the operator's command that is transferred from the input circuitry 22 and adjusts the voltage that is fed to the X-ray tube 12, thereby controlling on/off or the amount of X-rays that are emitted to the subject P. Furthermore, for example, the system controlling circuitry 21 controls the C-arm/table mechanism controlling circuitry 19 in accordance with an operator's command and adjusts the rotation and movement of the C arm 15 and the movement of the table 14. Moreover, for example, the system controlling circuitry 21 controls the collimator controlling circuitry 20 in accordance with an operator's command and adjusts the numerical aperture of the collimator blades included in the X-ray collimator 13, thereby controlling the irradiation area of X-rays that are emitted to the subject P.

Furthermore, the system controlling circuitry 21 controls image-data generation processing by the image-data generating circuitry 24, image processing by the image processing circuitry 26, analysis processing, or the like, in accordance with an operator's command. Moreover, the system controlling circuitry 21 controls the displays of the display 23a and the display 23b so as to present the GUI for receiving an operator's command, an image that is stored in the image-data storage circuitry 25, or the like. Furthermore, the system controlling circuitry 21 transmits, to an injector, a signal for starting or terminating injection of a contrast media, thereby controlling the injection of the contrast media.

Here, the operating terminal 200 in the X-ray angiography system 1 according to the first embodiment performs the above-described various controls in accordance with a command that is received by the user terminal 300. That is, the system controlling circuitry 21 according to the first embodiment performs various controls in accordance with a command that is received by the user terminal 300 in addition to an operator's command that is received by the input circuitry 22.

Figure 3:
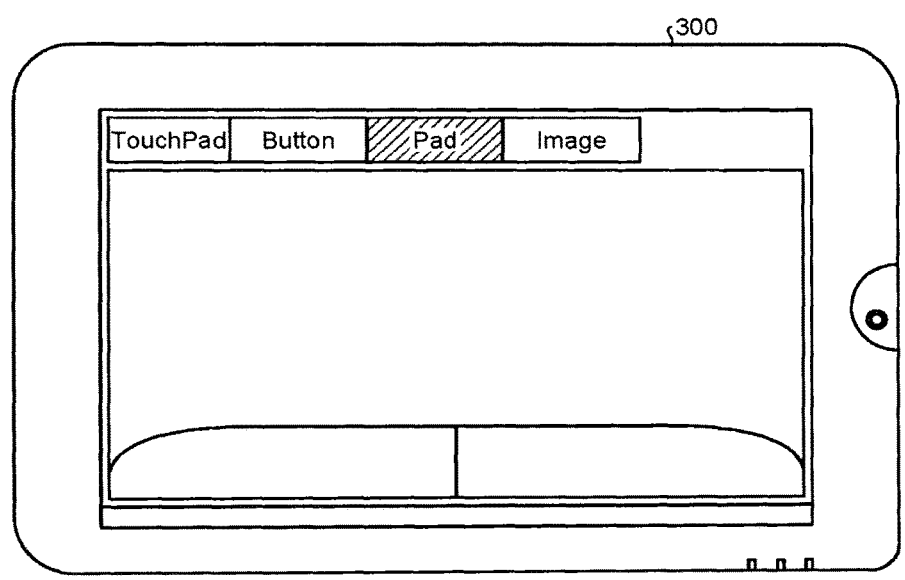
FIG. 3 is a diagram that illustrates an example of the user terminal according to the first embodiment.

FIG. 3 is a diagram that illustrates an example of the user terminal 300 according to the first embodiment. Here, FIG. 3 illustrates a perspective view of the user terminal 300. As illustrated in FIG. 3, for example, the user terminal 300 is a tablet PC on which various operations are performed by using a touch panel, and it is operated by a doctor, an assistant, a nurse, or the like.

For example, as illustrated in FIG. 3, the touch panel of the user terminal 300 is a touch-pad, and a doctor in the examination room R1 uses the touch-pad to operate the pointer that is presented on the examination-room display 23a, thereby performing an input operation on the GUI that is presented on the examination-room display 23a. Furthermore, as illustrated in FIG. 3, the user terminal 300 is capable of displaying "Image", or the like, that is presented on the examination-room display 23a or the operation-room display 23b.

Furthermore, as illustrated in FIG. 3, the user terminal 300 includes an in-camera that is on the same level as the touch panel. Moreover, in the user terminal 300, the touch panel can display the image, or the like, that is captured by the in-camera.

Figure 4:
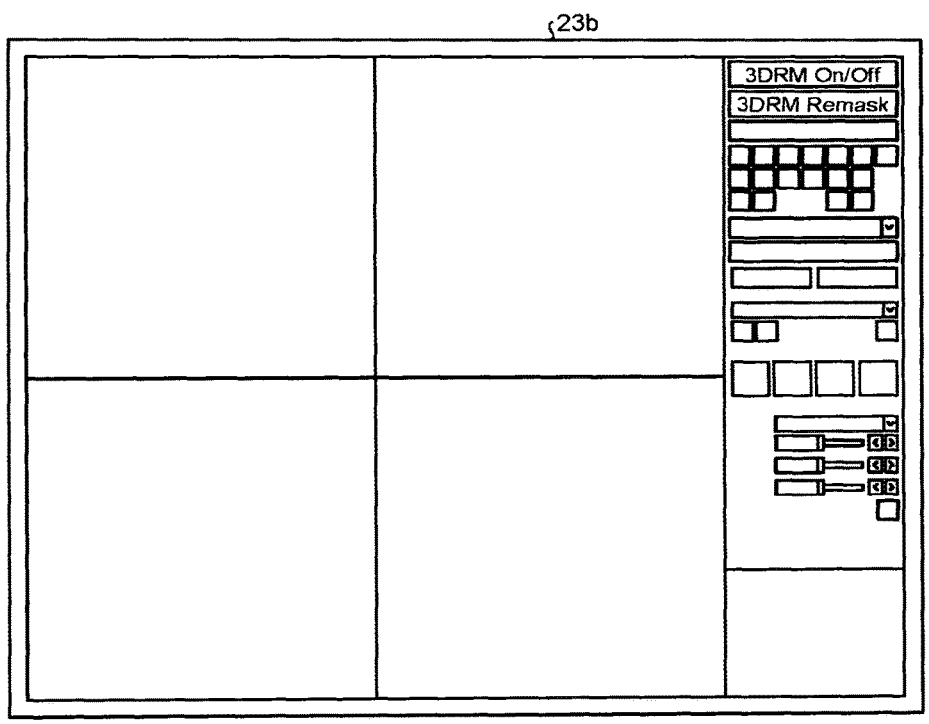
FIG. 4 is a diagram that illustrates an example of the screen that is the control target of the user terminal according to the first embodiment.

FIG. 4 is a diagram that illustrates an example of the screen that is the control target of the user terminal 300 according to the first embodiment. For example, as illustrated in FIG. 4, the control target of the user terminal 300 is the screen that includes operation areas and image display areas that are displayed on the display 23b of the operating terminal 200. For example, the user terminal 300 performs an operation that corresponds to each button in the operation area that is presented in the right-side area of FIG. 4.

As described above, the user terminal 300 receives various operations from an operator. The supporting device 50 according to the first embodiment can improve the operability of the above-described user terminal 300. Specifically, the supporting device 50 includes a holder, a supporter, and a controller (e.g. controlling circuitry), and the holder holds a user terminal 300 that includes a detection surface that detects an operator's input operation. The supporter is connected to the holder, and it is movably provided such that the user terminal 300 that is held by the holder is located at a predetermined position. When the detection surface detects an input operation, the controller fixes the supporter such that it is located at a predetermined position.

Figure 5:
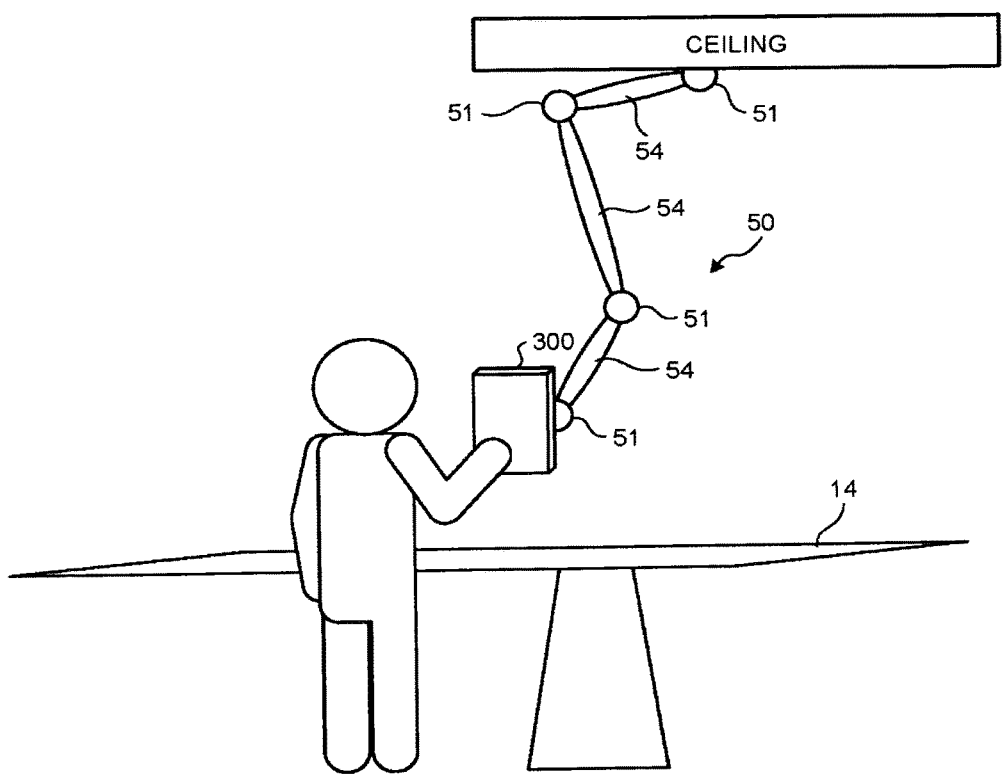
FIG. 5 is a diagram that illustrates an application example of a supporting device according to the first embodiment.

FIG. 5 is a diagram that illustrates an application example of a supporting device 50 according to the first embodiment. For example, as illustrated in FIG. 5, the supporting device 50 according to the first embodiment includes, as a supporter, arm sections 54 and joints 51 that are connected to the arm sections 54. The arm section 54 locates the user terminal 300, which is held by the holder, at a predetermined position. The joint 51 bends the arm section in an arbitrary direction. Furthermore, as illustrated in FIG. 5, for example, one end of the supporting device 50 connects to the ceiling, and the other end thereof holds the user terminal 300.

Figure 6:
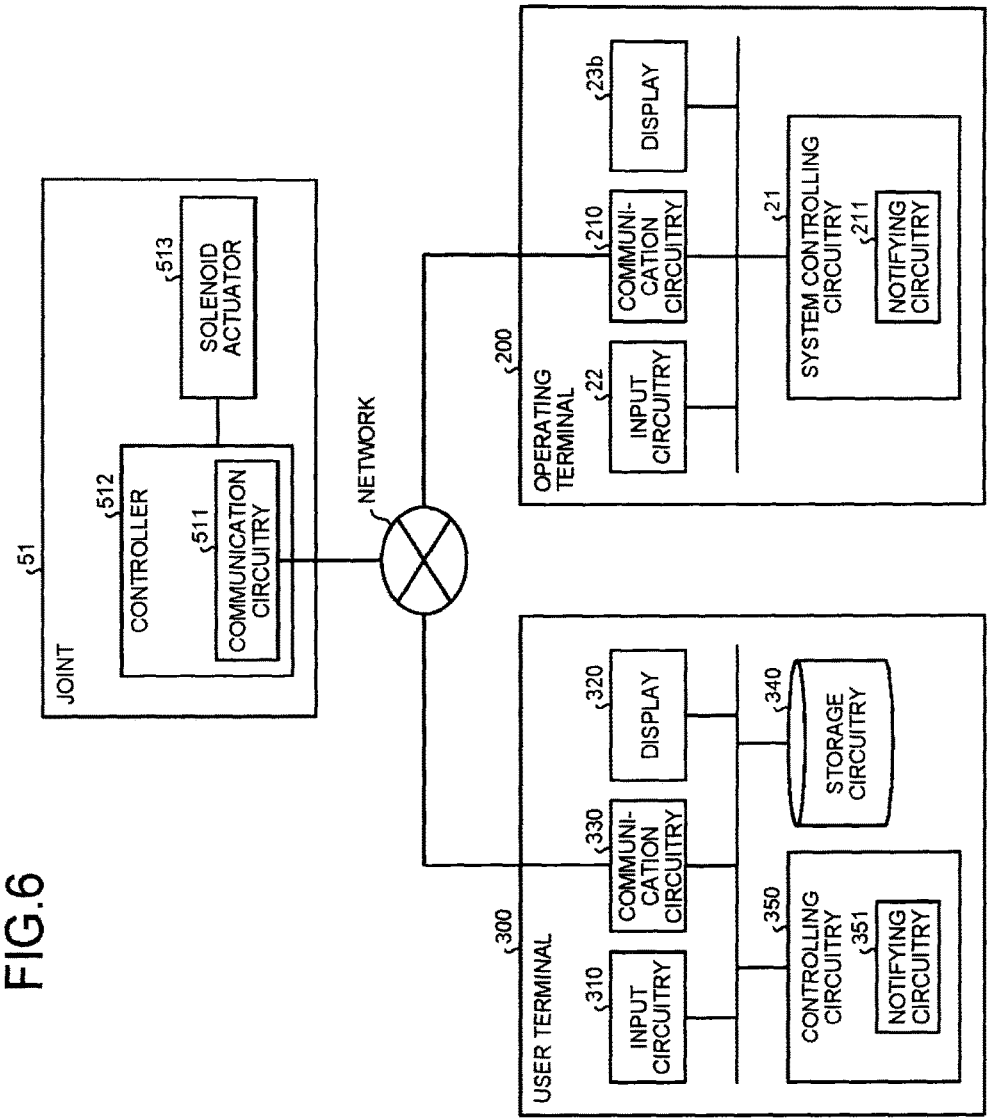
FIG. 6 is a diagram that illustrates an example of the configuration of a joint according to the first embodiment.

Here, the supporting device 50 according to the first embodiment is configured such that the joint 51 is fixed only during an operation, whereby the operability is improved. Specifically, a configuration is such that the joint 51 receives a signal from the user terminal 300 and it is fixed in accordance with the received signal. FIG. 6 is a diagram that illustrates an example of the configuration of the joint 51 according to the first embodiment.

As illustrated in FIG. 6, the joint 51 includes a communication circuitry 511, a controller 512, and a solenoid actuator 513, and it is connected to the user terminal 300 and the operating terminal 200 via a network. As illustrated in FIG. 6, the user terminal 300 includes an input circuitry 310, a display 320, a communication circuitry 330, a storage circuitry 340, and a controlling circuitry 350.

The input circuitry 310 is a touch panel that has an external shape like a flat plate, and it receives an input operation from an operator, such as a doctor or a nurse, who operates the user terminal 300. For example, the input circuitry 310 receives a touch operation, a flick operation, a swipe operation, or the like, thereby receiving various commands. Here, the input circuitry 310 is a capacitance type or pressure-sensitive type touch panel, and the sensitivity thereof is settable. For example, with the sensitivity of the input circuitry 310, it is possible to detect an operation before it is received.

The display 320 presents display information. For example, the display 320 is a display device, such as a liquid crystal panel, it is formed in combination with the input circuitry 310, and it displays the GUI for receiving an input operation by the input circuitry 310.

The communication circuitry 330 is a NIC, or the like, and it communicates with the joint 51 and the operating terminal 200 via a network. Specifically, the communication circuitry 330 performs various communications with the communication circuitry 511 of the joint 51 and a communication circuitry 210 of the operating terminal 200.

The storage circuitry 340 is, for example, a semiconductor memory device, such as a RAM or a flash memory, or a storage device, such as a hard disk or an optical disk, and it stores information, or the like, that is used by the controlling circuitry 350.

The controlling circuitry 350 is, for example, an electronic circuit, such as a central processing unit (CPU) or a micro processing unit (MPU), or an integrated circuit, such as an application specific integrated circuit (ASIC) or a field programmable gate array (FPGA), and it performs the overall control on the user terminal 300. As illustrated in FIG. 6, the controlling circuitry 350 includes a notifying circuitry 351. When the input circuitry 310 detects an input operation, the notifying circuitry 351 notifies the detection information to the joint 51 via the communication circuitry 330.

As illustrated in FIG. 6, the operating terminal 200 includes the communication circuitry 210 and a notifying circuitry 211 in addition to the input circuitry 22, the display 23b, and the system controlling circuitry 21. Although the image-data generating circuitry 24, the image-data storage circuitry 25, and the image processing circuitry 26 are not illustrated in FIG. 6, the operating terminal 200 actually includes the image-data generating circuitry 24, the image-data storage circuitry 25, and the image processing circuitry 26, as illustrated in FIG. 2.

As described above, the input circuitry 22 receives various input operations. Furthermore, as described above, the display 23b displays various types of information. The communication circuitry 210 is a network interface card (NIC), or the like, and it communicates with the joint 51 and the user terminal 300 via a network. Specifically, the communication circuitry 210 performs various communications with the communication circuitry 511 of the joint 51 and the communication circuitry 330 of the user terminal 300.

The system controlling circuitry 21 is, for example, an electronic circuit, such as a central processing unit (CPU) or a micro processing unit (MPU), or an integrated circuit, such as an application specific integrated circuit (ASIC) or a field programmable gate array (FPGA), and it performs the overall control on the X-ray angiography system 1, as described above. When X-rays are emitted or when a catheter is in operation, the notifying circuitry 211 notifies the information to the joint 51 via the communication circuitry 210.

The communication circuitry 511 receives the detection information from the notifying circuitry 351 of the user terminal 300. Furthermore, the communication circuitry 511 receives, from the notifying circuitry 211 of the operating terminal 200, the information that X-rays are emitted or the information that the catheter is in operation.

When the detection surface detects an input operation, the controller 512 fixes the joint 51. For example, when the communication circuitry 511 receives the detection information, the controller 512 operates the solenoid actuator 513 to fix the joint 51. Furthermore, when the communication circuitry 511 receives the information that X-rays are emitted or the information that the catheter is in operation, the controller 512 stops the operation of the solenoid actuator 513. Under the control of the controller 512, the solenoid actuator 513 fixes or unfixes the joint 51.

Here, the joint illustrated in FIG. 6 is only an example, and there is no limitation on the embodiment. For example, any mechanism may be used as long as it is a joint lock mechanism. That is, there may be a case where various electromagnetic locks that include the above-described solenoid actuator are used. In such a case, the controller 512 controls on/off of various electromagnetic locks as well as controlling the above-described solenoid actuator. Furthermore, there may be a case where a drive device, such as a motor, is used. In this case, too, the drive device fixes or unfixes the joint under the control of the controller 512.

Specifically, in the supporting device 50 illustrated in FIG. 5, when an operator tries to operate the user terminal 300, the operation is detected, the detection information is notified to the communication circuitry 511 of each of the joints 51, and each of the joints 51 is fixed. Thus, the user terminal 300 can be easily operated with one hand, and the operability is improved.

Figure 7A:
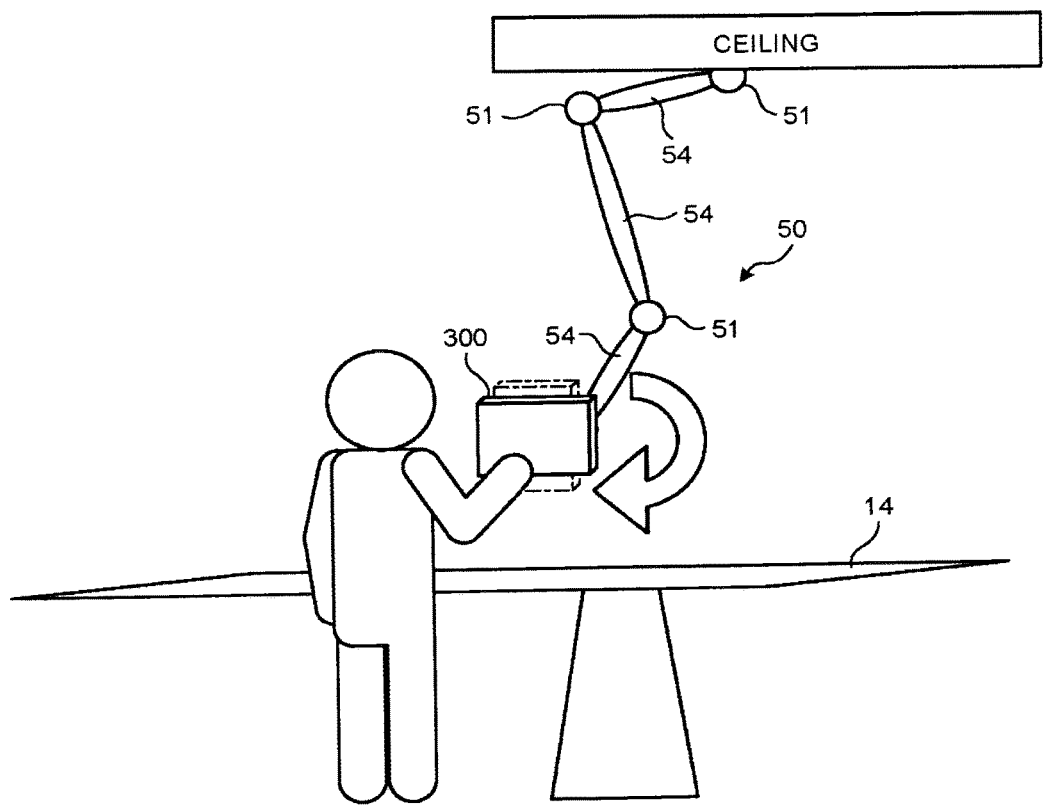
FIG. 7A is a diagram that illustrates an example of the supporting device according to the first embodiment.
Figure 7B:
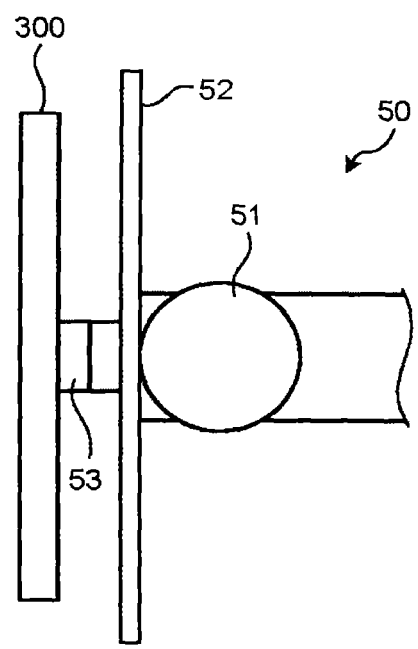
FIG. 7B is a diagram that illustrates an example of the supporting device according to the first embodiment.

Here, if there are the multiple joints 51, the controller 512 fixes the arbitrary joint 51 out of the multiple joints 51. FIG. 7A and FIG. 7B are diagrams that illustrate an example of the supporting device 50 according to the first embodiment. For example, with the supporting device 50 that is illustrated in FIG. 7A, when an operator tries to operate the user terminal 300, the operation is detected, and the detection information is notified to the communication circuitry 511 of the joint 51 of other than a joint 53 that holds the user terminal 300 so that each of the joints 51 is fixed. Therefore, as illustrated in FIG. 7A, the user terminal 300 can be rotated in a rotation direction in a flexible manner.

As for the above-described joint 53, as illustrated in FIG. 7B, for example, a holding plate 52 is provided just near the joint 51, and the rotatable joint 53 is provided between the user terminal 300 and the holding plate 52. Thus, even if the joint 51 is fixed, the user terminal 300 can rotate. The direction of an operation on the user terminal 300 is often the direction perpendicular to the operating surface of the user terminal 300; therefore, the above configuration hardly affects the operability.

Figure 8:
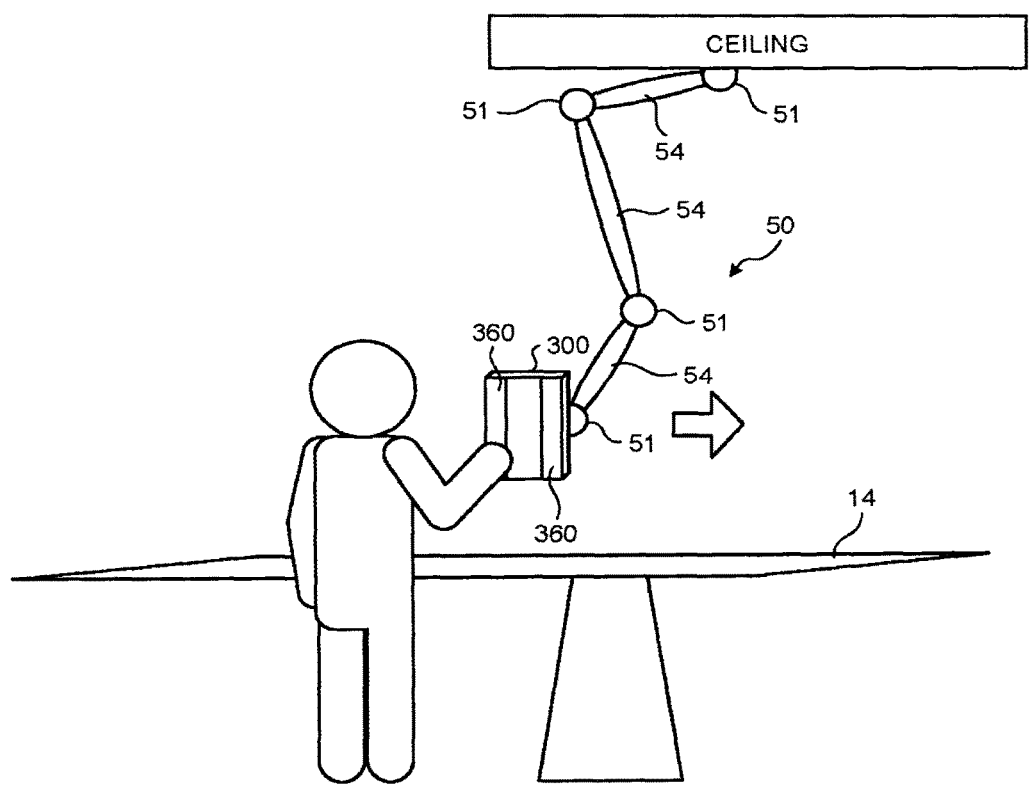
FIG. 8 is a diagram that illustrates an example of a detection area according to the first embodiment.

Here, with regard to the detection surface that detects an operator's input operation, the detection area for detecting the input operation can be arbitrarily set. FIG. 8 is a diagram that illustrates an example of the detection area according to the first embodiment. As illustrated in FIG. 8, for example, a non-detection area 360 can be set on the touch panel of the user terminal 300. Typically, in the case of a tablet PC, a large touch panel is designed. Hence, the area other than the touch panel is sometimes small; therefore, even if the user terminal 300 is to be moved, the detection surface is sometimes mistakenly touched and the joint is fixed. Thus, as illustrated in FIG. 8, the non-detection surface is set so that the above mistaken operation can be prevented.

Figure 9:
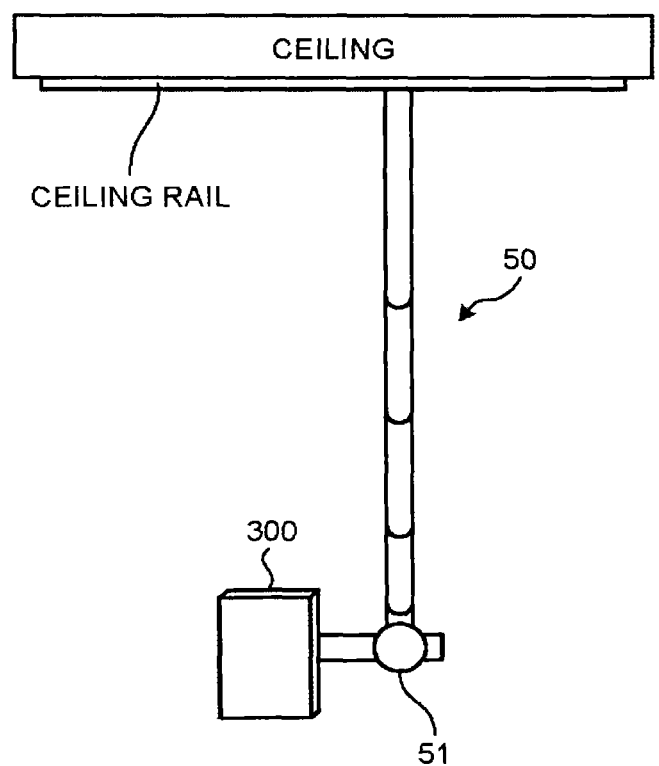
FIG. 9 is a diagram that illustrates an example of the supporting device according to the first embodiment.

Furthermore, the supporting device 50 according to the first embodiment can be configured such that the joint 51 is less likely to bend in an operating direction of an input operation. FIG. 9 is a diagram that illustrates an example of the supporting device 50 according to the first embodiment. For example, the supporting device 50 illustrated in FIG. 9 is configured such that it includes the single joint 51 and it is easily fixed in an operating direction of the user terminal 300. Specifically, the supporting device 50 illustrated in FIG. 9 is held by a ceiling rail and the number of joint shafts in an operating direction is reduced so that the user terminal 300 can be easily fixed.

Figure 10:
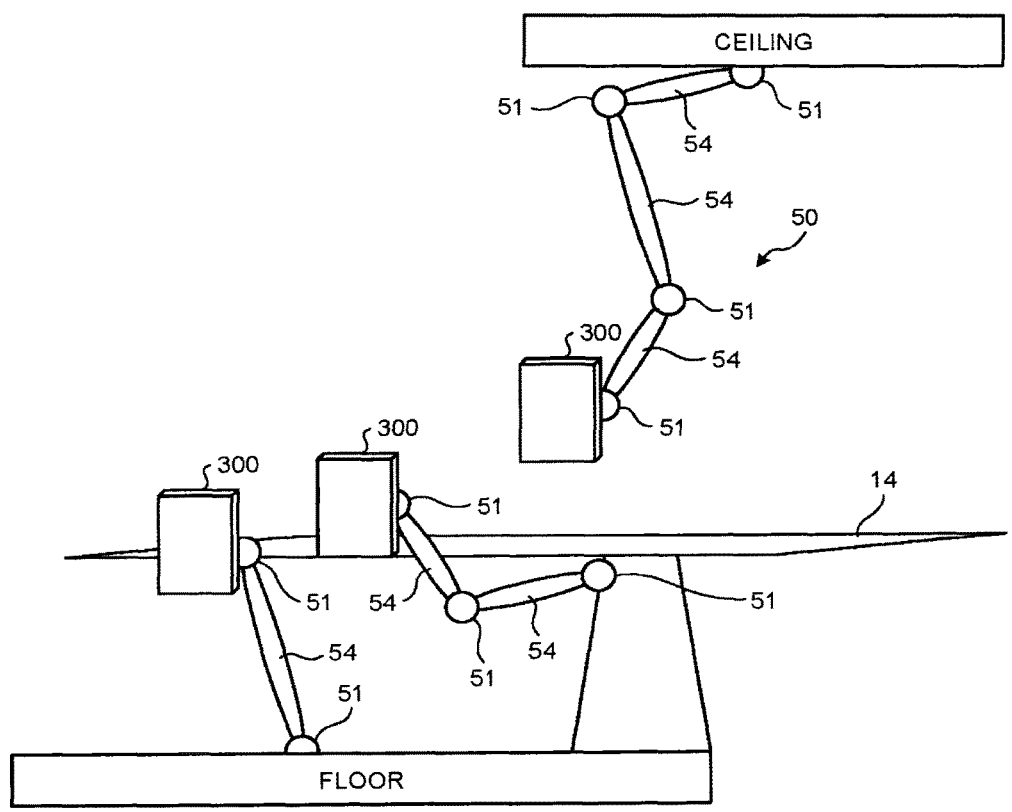
FIG. 10 is a diagram that illustrates an example of the supporting device according to the first embodiment.

In the same manner, the supporting device 50 illustrated in FIG. 10 is configured such that it is held by a floor surface, a bed, a ceiling, or the like, and the number of joints is reduced so that it is easily fixed in an operating direction of the user terminal 300. Here, FIG. 10 is a diagram that illustrates an example of the supporting device according to the first embodiment.

Figure 11:
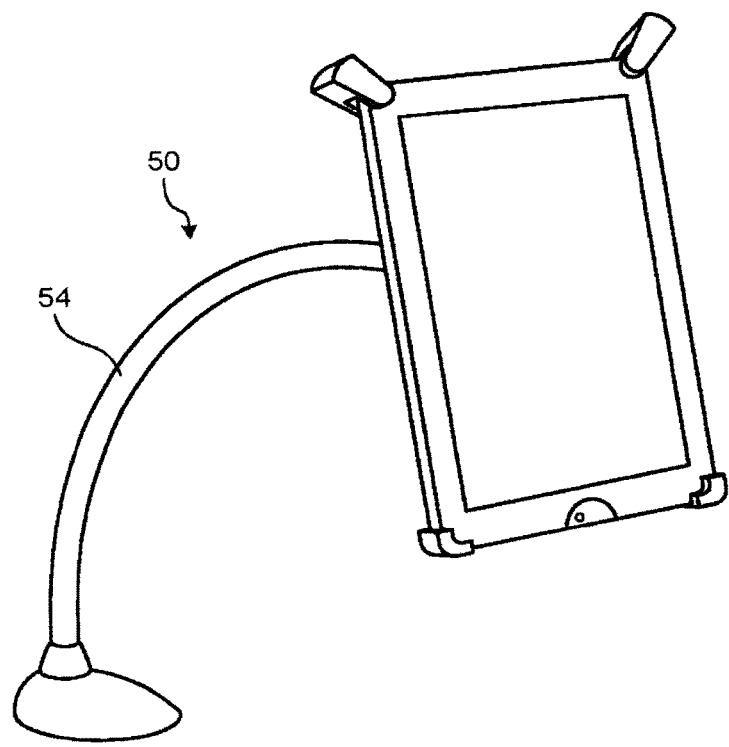
FIG. 11 is a diagram that illustrates a modified example of the supporting device according to the first embodiment.

In the above-described embodiment, an explanation is given of the supporting device 50 that includes the arm section 54 and the joint 51 as a supporter. However, there is no limitation on the embodiment, and there may be a case where the arm section 54 that has the same functionality as the joint 51 is used as a supporter. FIG. 11 is a diagram that illustrates a modified example of the supporting device 50 according to the first embodiment. For example, as illustrated in FIG. 11, the supporting device 50 includes a holder that holds a user terminal, the holder is connected to the arm section 54, and the other end of the arm section 54 is connected to a floor surface, a bed, or the like, for holding.

Here, in the supporting device 50 illustrated in FIG. 11, the arm section 54 has the same functionality as the above-described joint 51. For example, the arm section 54 is a flexible arm that can be bent in any direction in a flexible manner. Furthermore, the bent section of the arm section 54 is fixed or unfixed on the basis of the detection information from the user terminal 300, the information from the X-ray diagnostic apparatus that X-rays are being emitted, the information indicating that the catheter is in operation, or the like, as is the case with the above-described joint 51. Specifically, the bent section of the arm section 54 is fixed or unfixed by a drive device, such as a solenoid actuator or a motor.

Figure 12:
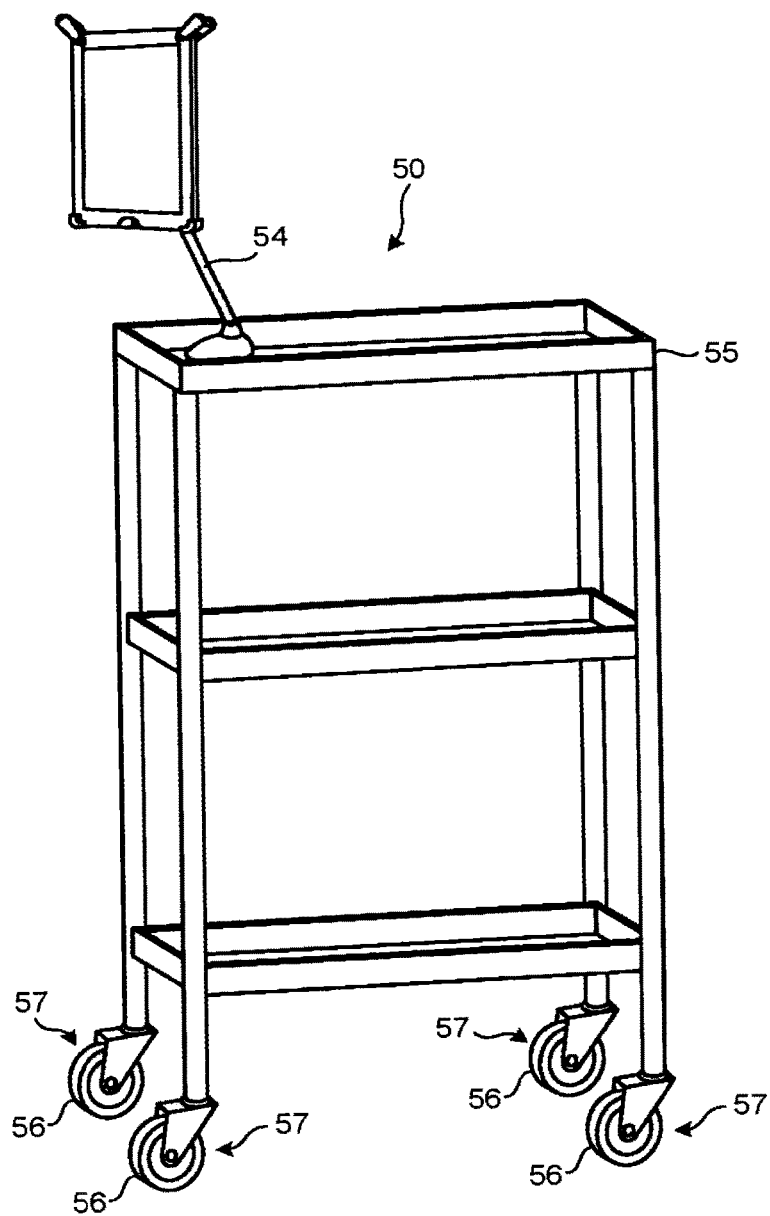
FIG. 12 is a diagram that illustrates a modified example of the supporting device according to the first embodiment.

Furthermore, in the above-described embodiment, an explanation is given of the supporting device 50 that includes the arm section 54 and the joint 51 as a supporter or the supporting device 50 that includes the arm section 54 (the flexible arm) as a supporter. However, there is no limitation on the embodiment, and there may be a case of a supporting device that includes, for example, a wagon with casters attached or a cart as a supporter. FIG. 12 is a diagram that illustrates a modified example of the supporting device 50 according to the first embodiment. For example, as illustrated in FIG. 12, the supporting device 50 includes the arm section 54, a main body section 55, wheels 56, and wheel controllers 57. The arm section 54 supports a user terminal, such as a tablet PC, and the main body section 55 supports the arm section 54. Furthermore, the main body section 55 includes the wheels 56 so that it is configured to be movable to any position.

The wheel controller 57 includes the above-described controller 512, and it controls the wheel 56 so as to fix it when the communication circuitry 511 receives the detection information or when the communication circuitry 511 receives the information that X-rays are emitted or the information that the catheter is in operation. For example, the wheel controller 57 is located inside the wheel 56, and it fixes the rotary shaft of the wheel 56 by using a drive device, such as a solenoid actuator or a motor, or cancels the fixed state. Thus, for example, during an operation on the tablet PC that is placed on the supporting device 50 that includes the wheels as illustrated in FIG. 12, it is possible to prevent simultaneous movements of the wheels 56, and the operability of the user terminal can be improved.

As described above, with the supporting device 50 according to the present application, when an operator tries to operate the user terminal 300, the operation is detected, the detection information is notified to the joints 51 and the communication circuitry 511 of the wheel controller 57, and each of the joints 51 and the wheel controller 57 are fixed. Here, in the supporting device 50, it is possible to perform a control so as to cancel the fixed states of the joint 51 and the wheel controller 57 after an input operation is performed by an operator. In such a case, for example, after a predetermined time elapses since an input operation is completed via the detection surface, the controller 512 cancels the fixed states of the joint 51, the arm section 54, and the wheel controller 57. Specifically, the controller 512 performs a control so as to unfix the joint 51, the arm section 54 (the flexible arm), and the wheel controller 57, which are fixed by the solenoid actuator, the motor, or the like. Thus, the supporting device 50 according to the present application makes it possible to move the user terminal 300 without performing an operation to cancel the fixed state of the supporter that is in the fixed state.

As described above, according to the first embodiment, the holder holds the terminal device that includes the detection surface that detects an operator's input operation. The supporter is connected to the holder and is bent in an arbitrary direction so that the terminal device, which is held by the holder, is located at a predetermined position. If an input operation is detected by the detection surface, the controller fixes the supporter such that it is bent in an arbitrary direction. Therefore, with the supporting device 50 according to the first embodiment, the position of the user terminal can be fixed when a user operates the user terminal, and the operability of the user terminal can be improved.

Furthermore, according to the first embodiment, the arm section 54 locates the user terminal, which is held by the holder, at a predetermined position. The joint 51 bends the arm section 54 in an arbitrary direction. When an input operation is detected by the detection surface, the controller 512 fixes the joint 51 in a state where the arm section is bent in the arbitrary direction. Therefore, with the supporting device 50 according to the first embodiment, it is possible to fix the joint, which is a movable section, when an operator operates the user terminal 300, and the operability of the user terminal can be improved.

Furthermore, according to the first embodiment, the detection surface is of a capacitance type or a pressure sensitive type that is settable to a predetermined sensitivity. Therefore, the supporting device 50 according to the first embodiment can be applied to various types of the user terminal 300.

Furthermore, according to the first embodiment, the detection area of the detection surface for detecting an operator's input operation can be set arbitrarily. Therefore, the supporting device 50 according to the first embodiment can reduce mistaken operations.

Furthermore, according to the first embodiment, if there are the multiple joints 51, the controller 512 fixes the arbitrary joint 51 out of the multiple joints 51. Therefore, the supporting device 50 according to the first embodiment makes it possible to handle various conditions in a flexible manner.

Furthermore, according to the first embodiment, the joint 51 is configured such that it is less likely to bend in an operating direction of an input operation. Therefore, the supporting device 50 according to the first embodiment makes it possible to easily fix the user terminal 300.

Moreover, according to the first embodiment, the controller 512 unfixes the joint 51 when X-rays are emitted by the X-ray diagnostic apparatus or when the catheter is in operation. Therefore, the supporting device 50 according to the first embodiment makes it possible to ensure that the joint 51 is unfixed when the user terminal 300 is not operated.

As described above, according to the first embodiment, the supporting device and the X-ray diagnostic apparatus according to the present embodiment make it possible to improve the operability of a user terminal.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A supporting device comprising:
a holder configured to hold a terminal device that includes a detection surface that detects an input operation by an operator;
a supporter configured to be connected to the holder and to be movably provided so as to locate the terminal device at a predetermined position, the terminal device being held by the holder; and
a controller configured to fix the supporter in a state where the supporter is located at a predetermined position when the detection surface detects the input operation.

2. The supporting device according to claim 1, wherein the controller cancels a fixed state of the supporter after a predetermined time elapses since the input operation is completed via the detection surface.

3. The supporting device according to claim 1, wherein the supporter includes:
an arm configured to locate a terminal device at a predetermined position, the terminal device being held by the holder; and
at least a joint configured to bend the arm in an arbitrary direction, and
when the detection surface detects the input operation, the controller fixes the joint in a state where the arm is bent in the arbitrary direction.

4. The supporting device according to claim 3, wherein, when the at least a joint includes multiple joints, the controller fixes an arbitrary joint out of the multiple joints.

5. The supporting device according to claim 3, wherein the joint is configured to be less likely to bend in an operating direction of the input operation.

6. The supporting device according to claim 3, wherein the controller unfixes the joint when an X-ray is emitted by an X-ray diagnostic apparatus or when a catheter is in operation.

7. The supporting device according to claim 1, wherein the detection surface is of a capacitance type or a pressure sensitive type that is settable to a predetermined sensitivity.

8. The supporting device according to claim 1, wherein a detection area of the detection surface for detecting an input operation by the operator is settable arbitrarily.

9. The supporting device according to claim 1, wherein the controller controls on/off of an electromagnetic lock.

10. An X-ray diagnostic apparatus comprising:
an X-ray emitting circuitry configured to emit an X-ray to a subject;
a holder configured to hold a terminal device that includes a detection surface that detects an input operation by an operator;
a supporter including a joint and configured to be connected to the holder and that to be bent in an arbitrary direction so as to locate the terminal device at a predetermined position, the terminal device being held by the holder; and
a controller configured to:
fix the supporter in a state where the supporter is bent in the arbitrary direction when the detection surface detects the input operation, and
unfix the joint when the X-ray emitting circuitry emits an X-ray.

* * * * *